United States Patent
Garriga I Rodo

(10) Patent No.: US 11,369,509 B2
(45) Date of Patent: Jun. 28, 2022

(54) APPLICATOR DEVICE FOR A MENSTRUAL CUP

(71) Applicant: ECAREYOU INNOVATION, S.L., Rubi (ES)

(72) Inventor: Joan Garriga I Rodo, Rubi (ES)

(73) Assignee: ECAREYOU INNOVATION, S.L, Barcelona (ES)

( * ) Notice: Subject to any disclaimer, the term of this patent is extended or adjusted under 35 U.S.C. 154(b) by 530 days.

(21) Appl. No.: 16/315,191

(22) PCT Filed: Jun. 23, 2017

(86) PCT No.: PCT/ES2017/070458
§ 371 (c)(1),
(2) Date: Jan. 4, 2019

(87) PCT Pub. No.: WO2018/115546
PCT Pub. Date: Jun. 28, 2018

(65) Prior Publication Data
US 2019/0151136 A1  May 23, 2019

(30) Foreign Application Priority Data
Jul. 13, 2016  (ES) .............................. ES201630904U

(51) Int. Cl.
*A61F 13/26* (2006.01)
*A61F 6/12* (2006.01)
(Continued)

(52) U.S. Cl.
CPC .............. *A61F 5/4553* (2013.01); *A61F 6/12* (2013.01); *A61F 13/15* (2013.01); *A61F 13/26* (2013.01)

(58) Field of Classification Search
CPC .... A61F 6/12; A61F 6/18; A61F 13/26; A61F 13/266; A61F 6/00; A61F 6/06;
(Continued)

(56) References Cited

U.S. PATENT DOCUMENTS

| | | | | | |
|---|---|---|---|---|---|
| 4,273,125 | A | * | 6/1981 | Sakurai | A61F 13/263 604/16 |
| 2009/0247930 | A1 | * | 10/2009 | Fung | A61F 13/266 604/16 |

FOREIGN PATENT DOCUMENTS

| | | | | |
|---|---|---|---|---|
| EP | 0616797 | A1 | 9/1994 | |
| GB | 1199901 | A * | 7/1970 | ............... A61F 6/08 |

(Continued)

OTHER PUBLICATIONS

International Search Report dated Oct. 23, 2017 for International Application No. PCT/ES2017/070458 filed Jun. 23, 2017.

*Primary Examiner* — Catharine L Anderson
(74) *Attorney, Agent, or Firm* — Blue Filament Law PLLC

(57) ABSTRACT

Two cylindrical parts (2, 3) are provided which are able to be coupled to each other with an axial sliding movement, of which, a first outer part (2) includes securing means (21) for the menstrual cup (4) to be placed, and a second inner part (3), which includes pushing means (31) which deploy the menstrual cup (4) from the securing means (21). The outer part (2) has an inner through hollow (22) suitable for receiving the inner part (3) in a fitted manner. The securing means (21) are made up of corresponding elastic arms which emerge parallel from the distal end (2*a*) of said part (2). The proximal end (2*b*) of the external part (2) has a smooth section (23). The appendages (31) of the inner part (3) have a perimeter edge and a length. The inner part (3) has an inner (Continued)

perforation (34) for inserting a thread-like element of the menstrual cup (4) as extraction means (4*a*).

13 Claims, 1 Drawing Sheet

(51) Int. Cl.
*A61F 5/455* (2006.01)
*A61F 13/15* (2006.01)

(58) Field of Classification Search
CPC .......... A61F 6/08; A61F 6/14; A61F 13/2045; A61F 13/263; A61F 5/4553
See application file for complete search history.

(56) References Cited

FOREIGN PATENT DOCUMENTS

| | | | |
|---|---|---|---|
| GB | 1199901 A | 7/1970 | |
| WO | 2014015975 A1 | 1/2014 | |
| WO | WO-2016156403 A1 * | 10/2016 | ........... A61K 31/565 |

\* cited by examiner

APPLICATOR DEVICE FOR A MENSTRUAL CUP

OBJECT OF THE INVENTION

The invention, as expressed by the title of the present specification, relates to an applicator device for menstrual cups, which provides a notable novelty in the current state of the art.

The object of the present invention is an applicator device, the purpose of which is to facilitate the operation of placing the menstrual cup in the body of the woman, making it more hygienic and quicker and, at the same time, preventing the need to introduce the fingers to do so, mechanizing the process and facilitating a correct placement.

FIELD OF APPLICATION OF THE INVENTION

The field of application of the present invention falls within the sector of the industry dedicated to manufacturing of accessories for intimate female hygiene items, particularly focusing on the sector of those intended to contain the menstrual flow, and even more particularly those known as menstrual cups.

BACKGROUND OF THE INVENTION

In the market there are diverse devices for containing menstrual flow known as menstrual cups and which essentially consist of a waterproof and flexible body, normally made of silicone, which adopts a vessel configuration as a cup, hence the name, in the lower outer portion thereof, the one opposite from the mouth, having securing means in order to proceed to the extraction thereof once used, which can consist of thickenings or, in more recent models, of a thread-like element.

However, the use thereof poses certain reservations, among which the fact that, for the placement thereof, there is no known accessory that facilitates this and it must be performed by manually introducing the mentioned body inside the vagina, attempting to keep the mouth oriented towards the inside and the extraction means oriented towards the opposite side, which, apart from not being very hygienic, can be complicated and cause errors in the placement which make the use thereof not very efficient, with the drawbacks that this brings with it.

Therefore, objective of the present invention is the development of a novel accessory specifically designed to prevent such drawbacks and provide practical and effective means for facilitating said placement of the menstrual cup, making it so the use thereof can reach a higher number of users.

Furthermore, and regarding the current state of the art, it should be noted that the applicant at least is unaware of the existence of any other applicator device for menstrual cups or invention for a similar application that has technical and structural characteristics that are the same as or similar to those that this invention claims.

DESCRIPTION OF THE INVENTION

Thus, the applicator device for menstrual cups proposed by the invention amounts to a noteworthy novelty within its field of application, since by employing it one may satisfactorily reach the aforementioned objectives, the characterising details that make is possible being duly recorded in the claims included at the end of the present description.

Specifically, that which proposes the invention, as indicated previously, is an applicator device specifically designed to facilitate the operation of placing a menstrual cup in the body of the woman so that it is more hygienic, quick and prevents errors.

To do so, the device is essentially configured starting from two parts which are able to be coupled to each other with an axial sliding movement comprising fastening means of the cup, in one of them, enabling the insertion thereof into the body of the woman, and, in the other, pushing means for the separation thereof from the fastening means and causing a correct placement.

More specifically, the device comprises an external part, hollow on the inside and provided on the distal end thereof with corresponding arms acting as a gripper, between which the cup is secured when placing it folded between them, and an internal part that, dimensioned to fit snugly into the inside of the external part, is slid inside the same by way of a piston, such that the sliding movement between both parts produces the pushing, by corresponding appendages provided on the distal end of said inner part, on the cup secured between the arms of the external part, facilitating the perfect placement thereof in the body of the woman.

Furthermore, it is worth mentioning that both parts are preferably hollow such that if the cup has, as securing means, a thread-like element, it can be inserted through the hollow of the inner part.

The described applicator device for menstrual cups base therefore consists of an innovative structure with characteristics heretofore unknown for its intended purpose, reasons which, taken together with its usefulness, provide it with sufficient grounds for obtaining the requested exclusivity privilege.

DESCRIPTION OF THE DRAWINGS

As a complement the present description, and for the purpose of helping to make the characteristics of the invention more readily understandable, the present specification is accompanied by a set of drawings, constituting an integral part of the same, which by way of illustration and not limitation represents the following.

PREFERRED EMBODIMENT OF THE INVENTION

Figure 1:
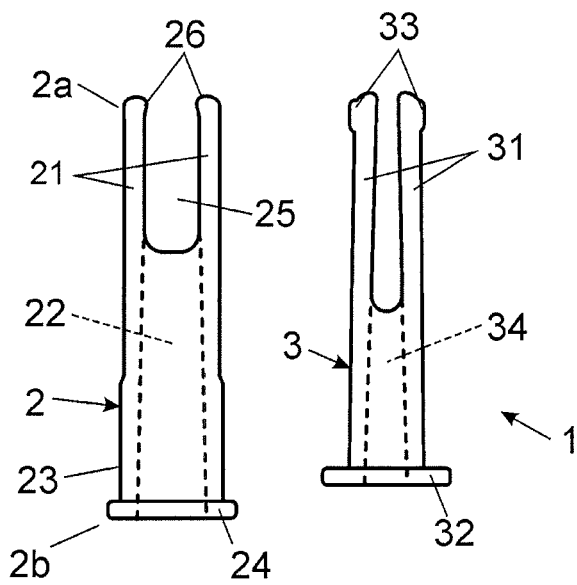
FIG. 1.—Shows an exploded side elevation view of an exemplary embodiment of the applicator device for menstrual cups, object of the invention, showing the portions and elements it comprises, as well as the configuration thereof.

In light of the aforementioned figures, and in accordance with the adopted numbering, one may observe therein a non-limiting embodiment of the applicator device for menstrual cups of the invention, which comprises the parts and elements indicated and described in detail below.

Thus, as seen in said figures, the device (1) in question essentially comprises two parts (2, 3) which are able to be coupled to each other with an axial sliding movement, of which, a first part, or outer part (2), comprises securing means (21) for the menstrual cup (4) to be placed, which enable the folded insertion thereof inside the body of the woman, and a second part, or inner part (3), which comprises pushing means (31) which deploy the menstrual cup (4) from the securing means (21) of the outer part (2) inside the body of the woman, causing the opening of the cup for the placement thereof, in an adequate position for the use thereof.

Figure 3:
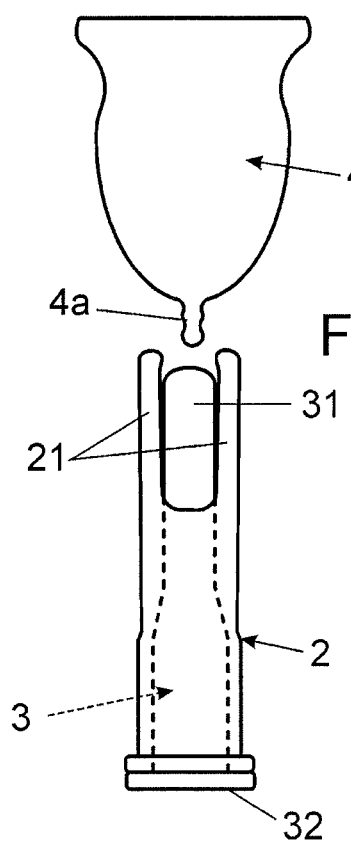
FIG. 3.—Shows an elevation view of the device, in the position thereof when in use once the cup has been placed.

As seen in FIG. 3, the menstrual cup (4) for which the device (1) is intended is made up of a flexible body, in the shape of a cup-like vessel, provided with extraction means (4a) in the external portion opposite from the mouth thereof, said extraction means (4a) being able to consist of protuberances, such as in the example shown, or in thread-like elements (not shown).

In the preferred embodiment, both parts are cylindrical and the outer part (2) has an inner through hollow (22) suitable for receiving the inner part (3) in a fitted manner enabling the axial sliding movement between both (2, 3).

In turn, the securing means (21) for the menstrual cup (4) that said external part (2) has are made up of corresponding arms (21) acting as a gripper proceeding parallel from one of the ends of said part (2), specifically from the end through which the device (1) is inserted into the body of the woman, which is indicated as the distal end (2a), while the opposite end, or proximal end (2b) of said external part (2) has a smooth section (23) in order to facilitate the handling thereof as well as, optionally, a protrusion (24).

More specifically, said arms (21) create a central housing (25) for the insertion of the cup (4) and have an appropriate length in order to equip them with a certain elasticity which causes them to act as a gripper. Optionally, the tips (26) of both arms (21) are slightly thicker towards the inner portion thereof.

Advantageously, the pushing means comprising the inner part (3), in order to deploy the menstrual cup (4) from the securing means (21) of the outer part (2), are made up of corresponding appendages (31) which emerge parallel from said inner part (3), which is inserted into the outer part (2) through the hole of the inner through hollow open at the proximal end (2b) thereof, while the opposite end of the inner part (3) has a perimeter edge (32) which acts as a stop preventing the insertion thereof further than what is necessary inside the outer part (2):

It is worth mentioning that, like the arms (21) of the outer part (2), the appendages (31) of this inner part also have a length such that they are provided with a certain elasticity, such that, upon being inserted inside the external part (2), they are joined together. Furthermore, the ends of both appendages (31) preferably have respective widenings (33) which determine a larger surface for pushing the menstrual cup (4).

Furthermore, the inner part (3) also preferably has an inner perforation (34) therein which passes through it longitudinally in order to, if applicable, insert a thread-like element which the menstrual cup (4) can have as extraction means (4a) therefrom.

Figure 2:
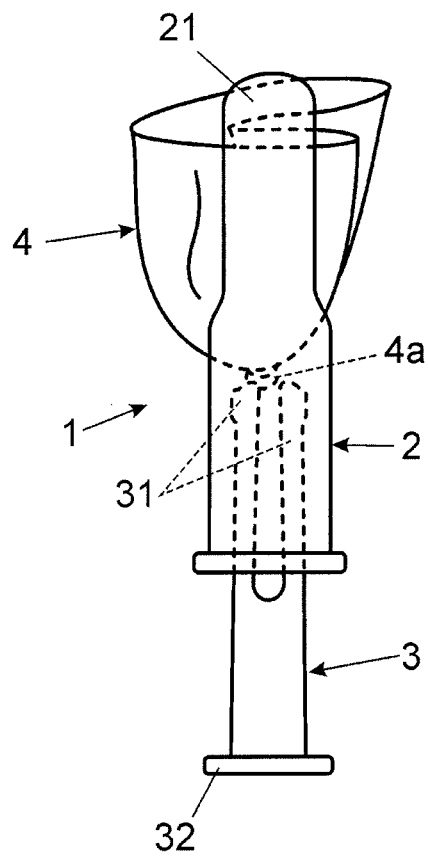
FIG. 2.—Shows an elevation view of the applicator device for menstrual cups, according to the example shown in FIG. 1, once assembled and in the position to hold the cup before the introduction thereof inside the body of the woman.

With all of this, the mode of use of the device is as follows:

Proceeding, firstly, after grasping the device of the invention (1), to the fastening of the menstrual cup (4) in the external part (2), placing it folded between the securing means (21) which it has on the distal end (2a) thereof, taking care to place the mouth of the cup oriented towards the end portion of said distal end (2a) and the extraction means (4a) thereof oriented towards the centre of the part (2), as shown in FIG. 2.

Then, the inner part (3) is partially introduced into the external part (2) through the hole of the inner through hollow (22) thereof. If the cup (4) has thread-like elements as extraction means (4a), these are inserted into the device (1) through the inner perforation (34) of the inner part (3), although this option has not been shown.

Then, the device (1) is introduced into the body of the user, inserting the menstrual cup (4) secured with the securing means (21) of the external part (2), which prevent it from being held with the fingers and prevent the need to introduce them inside the vagina, since only said outer part (2) is held.

Finally, once the cup has been introduced into the body of the woman, a relative axial displacing movement between both of them, such that by holding the inner part (3) and keeping it at a fixed distance from the body of the woman, the outer part (2) moves towards the outside, until being completely extracted, making the pushing means (31) of the inner part (3) work to keep the cup (4) placed in the position thereof inside the body, as shown by FIG. 3, until the device (1) is completely extracted. In the case of the menstrual cup (4) having thread-like elements as extraction means (4a), before performing the relative axial displacement between the parts (3 and 2), the user must grip the end of the thread-like element which protrudes from the inner perforation (34) of the inner part (3) with the aim of ensuring a correct placement of the menstrual cup (4).

Having sufficiently described the nature of the present invention, as well as the ways of implementing it, it is not considered necessary to extend its explanation for any expert in the state of the art to understand its scope and the advantages which derive from it, specifying that, within its essence, it can be carried out in other embodiments that differ in detail from the one provided by way of example, and which are also covered by the requested protection, provided that they do not alter, change or modify its fundamental principle.

The invention claimed is:

1. An applicator device for menstrual cups, the menstrual cup made up of a flexible cup-shaped body (4) having a mouth and provided with an extractor (4 a) having protuberances or thread-like elements located on an external portion opposite from the mouth thereof, the applicator device characterized in that it comprises two parts (2, 3) comprising an outer part (2) and an inner part (3) which are able to be coupled to each other with an axial sliding movement, wherein both the outer part (2) and the inner part (3) are cylindrical and the outer part (2) has an inner through hole (22) configured to receive the inner part (3) in a fitted manner enabling the axial sliding movement between them, of which, the outer part (2) comprises two parallel distal extending securing arms (21) configured to grip the menstrual cup (4) to be placed, for the folded insertion thereof inside a body of a user, and the inner part (3) comprises two separate parallel distal extending pushing appendages (31) which deploy the menstrual cup (4) from the securing arms (21) of the outer part (2) once placed inside the body of the user by axially pushing the menstrual cup (4) with distal ends of the two separate parallel distal extending pushing appendages.

2. The applicator device for menstrual cups according to claim 1, characterised in that a proximal end (2 b) of the outer part (2) has a smooth section (23) in order to facilitate the handling thereof.

3. The applicator device for menstrual cups according to claim 2, characterised in that the securing arms (21) create a central housing (25) for the insertion of the cup (4) and have a length suitable to equip them with elasticity so that they act as a gripper.

4. The applicator device for menstrual cups according to claim 3, characterised in that the pushing appendages (31) comprised by the inner part (3) consist of corresponding appendages (31) which emerge parallel from a first end of the inner part (3), the inner part (3) configured to be inserted into the outer part (2) through the inner through hole (22) at the proximal end (2 b) thereof.

5. The applicator device for menstrual cups according to claim 4, characterised in that an opposite end of the inner part (3) from the end incorporating the pushing appendages (31) has a perimeter edge (32) acting as a stop.

6. The applicator device for menstrual cups according to claim 2, characterised in that the pushing appendages (31) comprised by the inner part (3) consist of corresponding appendages (31) which emerge parallel from a first end of the inner part (3), the inner part (3) configured to be inserted into the outer part (2) through the inner through hole (22) at the proximal end (2 b) thereof.

7. The applicator device for menstrual cups according to claim 6, characterised in that an opposite end of the inner part (3) from the end incorporating the pushing appendages (31) has a perimeter edge (32) acting as a stop.

8. The applicator device for menstrual cups according to claim 1, characterised in that an opposite end of the inner part (3) from the end incorporating the pushing appendages (31) has a perimeter edge (32) acting as a stop.

9. The applicator device for menstrual cups according to claim 1, characterised in that the appendages (31) of the inner part (3) have a length such that they are provided with elasticity.

10. The applicator device for menstrual cups according to claim 1, characterised in that free ends of both appendages (31) have respective widenings (33).

11. The applicator device for menstrual cups according to claim 1, characterised in that the inner part (3) has an inner perforation (34) therein which passes through it longitudinally in order to, if applicable, insert a thread-like element of the menstrual cup (4) as the extractor (4 a) therefrom.

12. The applicator device for menstrual cups according to claim 1, characterised in that the pushing appendages (31) comprised by the inner part (3) consist of corresponding appendages (31) which emerge parallel from a first end of the inner part (3), the inner part (3) configured to be inserted into the outer part (2) through the inner through hole (22) at a proximal end (2 b) thereof.

13. The applicator device for menstrual cups according to claim 12, characterised in that an opposite end of the inner part (3) from the end incorporating the pushing appendages (31) has a perimeter edge (32) acting as a stop.

* * * * *